(12) United States Patent
Stiger et al.

(10) Patent No.: US 10,722,689 B2
(45) Date of Patent: Jul. 28, 2020

(54) GUIDEWIRE WITH INTEGRAL RADIOPAQUE MARKERS

(71) Applicant: Medtronic Vascular, Inc., Santa Rosa, CA (US)

(72) Inventors: Mark Stiger, Windsor, CA (US); Richard Thomas, Cloverdale, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 690 days.

(21) Appl. No.: 15/149,882

(22) Filed: May 9, 2016

(65) Prior Publication Data

US 2016/0250450 A1    Sep. 1, 2016

Related U.S. Application Data

(62) Division of application No. 13/418,092, filed on Mar. 12, 2012, now Pat. No. 9,358,370.

(51) Int. Cl.
| | |
|---|---|
| *A61B 5/00* | (2006.01) |
| *A61M 25/09* | (2006.01) |
| *A61L 31/02* | (2006.01) |
| *A61L 31/14* | (2006.01) |
| *A61L 31/18* | (2006.01) |
| *C23F 4/00* | (2006.01) |

(52) U.S. Cl.
CPC ........... *A61M 25/09* (2013.01); *A61L 31/022* (2013.01); *A61L 31/146* (2013.01); *A61L 31/18* (2013.01); *C23F 4/00* (2013.01); *A61M 2025/09075* (2013.01); *A61M 2025/09108* (2013.01); *A61M 2025/09133* (2013.01); *A61M 2025/09166* (2013.01)

(58) Field of Classification Search
CPC .. A61B 2090/3966; A61B 2018/00404; A61B 2017/2217; A61F 2250/0098; A61F 2002/016; A61F 2/954; A61M 25/09; A61M 2025/1081; A61M 25/0662
USPC ........................ 600/585; 604/529; 216/39, 58
See application file for complete search history.

(56) References Cited

U.S. PATENT DOCUMENTS

| | | | |
|---|---|---|---|
| 4,719,924 A * | 1/1988 | Crittenden | ...... A61M 25/09033 600/434 |
| 5,106,455 A | 4/1992 | Jacobsen et al. | |
| 5,776,100 A * | 7/1998 | Forman | ................. A61M 25/09 604/102.03 |
| 6,107,004 A | 8/2000 | Donadio | |

(Continued)

*Primary Examiner* — May A Abouelela
(74) *Attorney, Agent, or Firm* — Medler Ferro Woodhouse & Mills PLLC (57) ABSTRACT

Embodiments hereof relate to a guidewire formed from an elongated shaft, at least a portion of the shaft having an outer layer, a plurality of channels formed through the outer layer, and an inner core. The outer layer is formed from a material non susceptible to erosion by an erosion agent and the inner core is formed from a radiopaque material susceptible to erosion by the erosion agent. When exposed to the erosion agent, core material adjacent to the channels is removed to form a pattern of integral radiopaque segments or markers with a plurality of voids therebetween. By controlling the location of channels and the rate of erosion of the core material, the pattern of integral radiopaque segments and voids allow for in situ measurement when viewed under fluoroscopy.

20 Claims, 4 Drawing Sheets

(56) References Cited

U.S. PATENT DOCUMENTS

| | | | |
|---|---|---|---|
| 6,387,060 B1* | 5/2002 | Jalisi | A61M 25/0043 600/585 |
| 6,620,114 B2 | 9/2003 | Vrba et al. | |
| 6,636,758 B2 | 10/2003 | Sanchez et al. | |
| 7,806,837 B2 | 10/2010 | Rasmussen et al. | |
| 7,878,984 B2* | 2/2011 | Jacobsen | A61M 25/0013 600/585 |
| 8,419,658 B2* | 4/2013 | Eskuri | A61M 25/09 600/585 |
| 8,556,914 B2* | 10/2013 | Vrba | A61M 25/00 606/127 |
| 9,339,632 B2* | 5/2016 | Eidenschink | A61M 25/10 |
| 9,387,308 B2* | 7/2016 | Hinchliffe | A61M 25/09 |
| 9,616,195 B2* | 4/2017 | Lippert | A61M 25/0013 |
| 9,808,595 B2* | 11/2017 | Turnlund | A61M 25/0013 |
| 2001/0049549 A1 | 12/2001 | Boylan et al. | |
| 2001/0054599 A1 | 12/2001 | Engelhardt | |
| 2002/0030796 A1 | 3/2002 | Anderson et al. | |
| 2003/0167052 A1 | 9/2003 | Lee et al. | |
| 2004/0167440 A1* | 8/2004 | Sharrow | A61M 25/0108 600/585 |
| 2004/0181174 A2* | 9/2004 | Davis | A61M 25/0013 600/585 |
| 2006/0121218 A1* | 6/2006 | Obara | A61L 29/085 428/34.7 |
| 2006/0189896 A1* | 8/2006 | Davis | A61M 25/0013 600/585 |
| 2007/0135732 A1 | 6/2007 | Dixon et al. | |
| 2009/0112127 A1* | 4/2009 | Keating | A61M 25/09 600/585 |
| 2009/0254000 A1* | 10/2009 | Layman | A61M 25/0068 600/585 |
| 2010/0010476 A1* | 1/2010 | Galdonik | A61B 17/221 604/529 |
| 2010/0063479 A1 | 3/2010 | Merdan et al. | |
| 2010/0145308 A1 | 6/2010 | Layman et al. | |
| 2010/0305475 A1* | 12/2010 | Hinchliffe | A61M 25/09 600/585 |
| 2011/0118628 A1* | 5/2011 | Zhou | A61M 25/09 600/585 |
| 2011/0144689 A1 | 6/2011 | Isch et al. | |
| 2011/0301686 A1* | 12/2011 | Bowman | A61B 17/12027 623/1.11 |
| 2012/0203207 A1* | 8/2012 | Northrop | A61M 25/09 604/529 |
| 2012/0244715 A1 | 9/2012 | Lebouitz et al. | |

* cited by examiner

FIG. 3

GUIDEWIRE WITH INTEGRAL RADIOPAQUE MARKERS

RELATED APPLICATIONS

This application is a Divisional of U.S. patent application Ser. No. 13/418,092, filed Mar. 12, 2012, now allowed, the disclosure of which is herein incorporated by reference in its entirety.

FIELD OF THE INVENTION

Embodiments hereof are directed to a guidewire having integral radiopaque markers formed therein.

BACKGROUND OF THE INVENTION

Medical guidewires are used in numerous catheterization procedures as an aid to placement of a catheter and/or prosthesis at a selected site within a body lumen. The catheter is constructed to perform a particular procedure at that internal site. Among the more common uses of guidewire is in the catheterization of blood vessels for diagnostic or therapeutic purposes. In such a vascular catheterization procedure, the guidewire is inserted, usually percutaneously, into one of the patient's blood vessels and is manipulated and advanced through the branches of the vascular system to the target site. The diagnostic or treatment catheter is then threaded over and advanced along the guidewire, with the guidewire serving to guide the catheter directly to the target site.

Often, use of a measuring or marker catheter is required to accurately determine the length of vasculature that requires treatment prior to insertion of the diagnostic or treatment catheter. More particularly, after the guidewire is positioned within the vasculature, a marker catheter is passed over the guidewire to the site of treatment. The marker catheter is provided with a plurality of radiopaque marker bands that are utilized to make in situ measurements and determine the length of vasculature that requires treatment. The marker catheter is removed. With the measurements, the appropriate size of an implant or prosthesis required for the treatment site may be selected. An implant or prosthesis which may be utilized in treatment or diagnostics of the treatment site may be a stent, a stent graft, a filter, an occlusion device or other implantable device. The selected implant is then delivered to the treatment site using a second catheter that is passed over the indwelling guidewire.

As endovascular interventional therapies have increased in popularity, physicians desire to treat their patients more efficiently. For example, physicians desire to reduce the impact to the patient from the interventional or operation standpoint. The exchange of several catheter devices as described above impacts the patient, and in some cases of tortuous vasculature, reduces patient baseline. A patient's baseline typically refers to a patient's condition prior to a clinical procedure or intervention, and thus is the control used for comparison purposes after the clinical treatment is applied. In regards to a clinical treatment utilizing a catheter, the catheter may cause damage to the patient's vessels during introduction, tracking, and manipulation. Thus, the exchange of several catheter devices may yield more or additional damage or irritation to the areas of contact, including the introduction site and internal surfaces of vessels. In addition to reducing patient impact, it is also desirable to reduce costs associated with an interventional procedure such as operating time and the number of devices required per procedure. Embodiments hereof are related to a guidewire that combines the delivery guidewire and the dimensioning catheter in order to reduce patient impact and costs associated with an endovascular interventional procedure.

BRIEF SUMMARY OF THE INVENTION

Embodiments hereof relate to a method of manufacturing a guidewire having a plurality of integral radiopaque markers formed therein. The method includes providing an elongated wire having an outer layer and an inner core, wherein the inner core is formed from a radiopaque material susceptible to erosion by an erosion agent and the outer layer is formed from a material non susceptible to erosion by the erosion agent. Channels are formed through the outer layer to expose the inner core. Via the channels, the inner core is subjected to the erosion agent and segments of the inner core adjacent to the channels are eroded, thereby forming a plurality of integral radiopaque markers and a plurality of voids therebetween.

Embodiments hereof also relate to a guidewire formed from an elongated shaft having an outer layer and an inner core. The inner core is formed from a radiopaque material susceptible to erosion by an erosion agent and the outer layer is formed from a material non susceptible to erosion by the erosion agent. The inner core is solid and continuous along a proximal portion of the shaft but the inner core is non-continuous along a marker portion of the shaft. The marker portion of the shaft includes a plurality of segments of the radiopaque material with a plurality of voids therebetween. The marker portion is distal to the proximal portion of the shaft.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

DETAILED DESCRIPTION OF THE INVENTION

Specific embodiments of the present invention are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician. In addition, the term "erode" or "erosion" of inner core material as utilized herein is intended to encompass erosion, corrosion, disintegration, dissolution, or similar methodologies in which a particular processing material, hereinafter referred to as a "erosion agent," removes finite amounts or segments of a material.

The following detailed description is merely exemplary in nature and is not intended to limit the invention or the application and uses of the invention. Although the description of the invention is in the context of treatment of blood vessels such as the aorta, coronary, carotid and renal arteries, the invention may also be used in any other body passageways where it is deemed useful. Furthermore, there is no intention to be bound by any expressed or implied theory presented in the preceding technical field, background, brief summary or the following detailed description.

Figure 1:
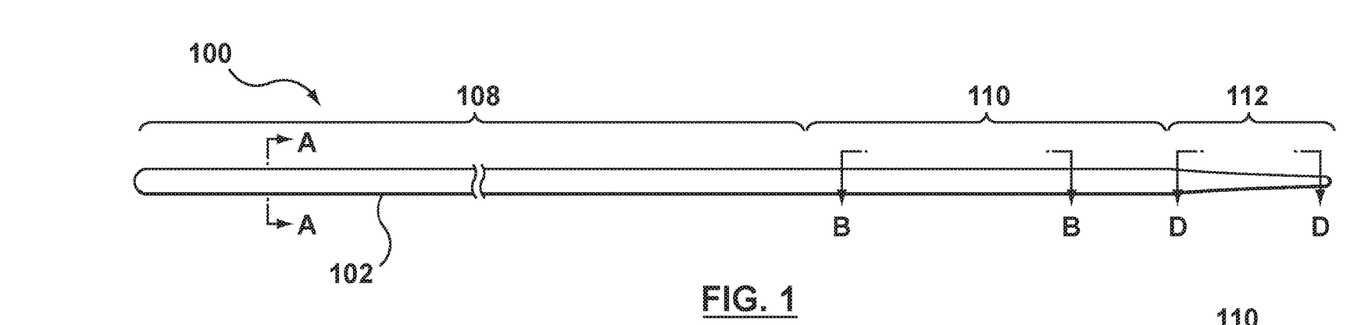
FIG. 1 is a side view of an embodiment of a guidewire having a marker portion with a plurality of integral radiopaque markers.

Embodiments hereof relate to a guidewire having integral radiopaque markers formed therein for making in-situ measurements. More particularly, FIG. 1 illustrates a steerable guidewire 100 which includes a proximal portion 108, a distal tip portion 112, and an intermediate marker portion 110 extending therebetween. As shown in the sectional view of FIG. 1B, marker portion 110 includes a series of integral radiopaque segments or markers 118 having voids or gaps 116 therebetween. Integral radiopaque markers 118 are visible under fluoroscopy and may thus be utilized for intravascular measurement, as well as assisting in alignment against or co-axial to a vessel wall. By including a series of integral radiopaque markers 118, guidewire 100 combines a delivery guidewire and a marker or measurement catheter into a single device. A guidewire having a series of integral radiopaque markers for measurement simplifies clinical procedures by reducing the amount of device exchanges in and out of the patient. Further, integral radiopaque markers 118 are positioned within, i.e., in the interior of, guidewire 100. Such interior radiopaque markers have several advantages over radiopaque markers that are attached to an exterior surface of an intravascular device, including both guidewires or catheters. Namely, exterior radiopaque markers must be held in position which requires extra manufacturing steps, may require a cover or coating to isolate the markers from the exterior or tracking surface of the guidewire, and may have reliability concerns because the exterior radiopaque markers may dislodge or cause hold-up of the intravascular device. Conversely, radiopaque markers 118 are integrally formed as a part of guidewire 100 and do not require any component or structure to hold markers 118 in place. Further, by forming radiopaque markers 118 within or interior to guidewire 100, the exterior or tracking surface of guidewire 100 is smooth and radiopaque markers 118 are isolated from the tracking surface without any additional manufacturing steps.

Guidewire 100 is formed from an elongated guidewire shaft 102 which is a coextruded or composite wire having an inner core 106 and an outer shell or layer 104. The materials of inner core 106 and outer layer 104 provide guidewire shaft 102 with sufficient column strength to be pushed through a patient's vascular system without kinking and also with enough flexibility to avoid damaging the blood vessel or other body lumen through which guidewire 100 is advanced. Further, guidewire 100 has the flexibility and strength required to intravascularly deliver a therapeutic or diagnostic device such as a catheter. Each material utilized for inner core 106 and outer layer 104 has different properties which either attenuate x-ray radiation or provide strength to guidewire 100. More particularly, the material for inner core 106 is a radiopaque material, thus visible under x-ray or fluoroscopic imaging equipment, while the material for outer layer 104 provides sufficient strength and flexibility to guidewire 100.

In addition to the material requirements of radiopacity and strength, the material of inner core 106 is susceptible to erosion by an erosion agent while the material of outer layer 104 is not susceptible to erosion by the erosion agent. Stated another way, the material of inner core 106 is a sacrificial material that can be removed by a process that does not damage the material of outer layer 104. By possessing different properties to be either susceptible or immune to erosion by the erosion agent, a series of integral radiopaque markers 118 may be formed within marker region 110 of guidewire 100 as will be described in more detail herein. Non-exhaustive examples of the material of inner core 106 include but are not limited to tungsten, tantalum, platinum, platinum and iridium alloy, rhenium, gold, molybdenum, silver, and alloys containing one or more thereof. Non-exhaustive examples of the material of outer layer 104 include but are not limited to stainless steel alloys, chromium cobalt alloys, and nickel titanium alloys such as Nitinol. Exemplary combinations of materials for the inner core, the outer layer, and the erosion agent are discussed in more detail herein with respect to FIG. 3.

Figures 1A, 1B, 1C:
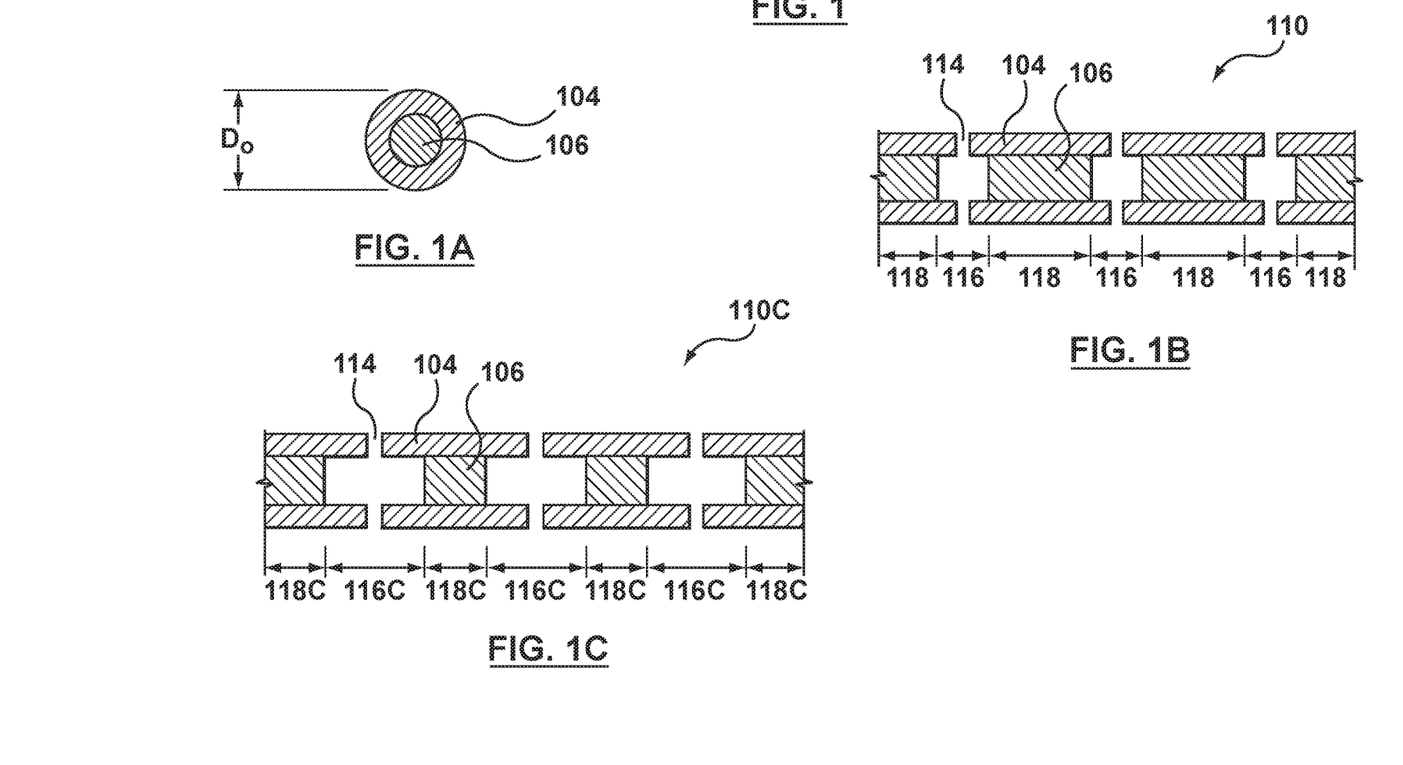
FIG. 1A is a cross-sectional view taken along line A-A of FIG. 1 within a proximal portion of the guidewire.
FIG. 1B is a sectional view taken along line B-B of FIG. 1 within a marker portion of the guidewire.
FIG. 1C is a sectional view taken along line B-B of FIG. 1, illustrating another embodiment of a marker portion of a guidewire.

As shown in the sectional view of FIG. 1A, proximal portion 108 is formed from the coextruded or composite wire having outer layer 104 and a solid or continuous inner core 106. An outer diameter $D_O$ of guidewire shaft 102 along proximal portion 108 may be constant. In one embodiment, outer diameter $D_O$ is 0.014 inch, 0.018 inch, or 0.035 inch although other dimensions are possible. The relative thicknesses of inner core 106 and outer layer 104 vary depending on the application, specific requirements for flexibility, specific requirements of treatment or diagnostic devices delivered there over, and/or desired radiopacity levels. In one embodiment, the thickness of outer layer 104 ranges from 50 to 90 percent of the cross-sectional diameter of the wire. In another embodiment (not shown), at least a portion of proximal portion 108 may include only a single, solid material. More particularly, the coextruded or composite wire utilized for guidewire shaft 102 may include a transition area within proximal portion 108 in which the material for outer layer 104 becomes the only material of guidewire shaft 102 and the material for inner core 106 is no longer present. Such a portion having only a single, solid material may be positioned in regions of the guidewire where inflexibility is desired and radiopacity is not desired, such as the most proximal portion of the guidewire. Such portions may be integral with the remainder of the guidewire shaft or may be a separate piece connected to the remainder of the guidewire through welding or other appropriate mechanical connections.

Figure 1D:
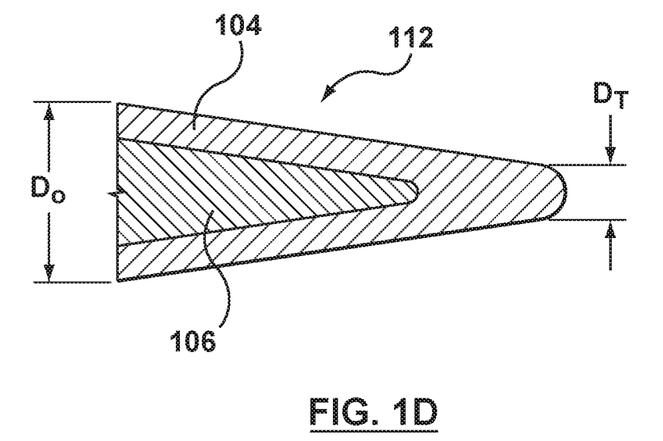
FIG. 1D is a cross-sectional view taken along line D-D of FIG. 1 within a distal tip portion of the guidewire.
Figure 1E:
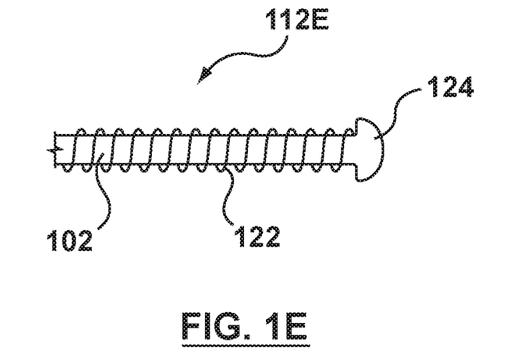
FIG. 1E is a side view illustrating another embodiment of a distal tip portion of a guidewire.
Figure 1F:
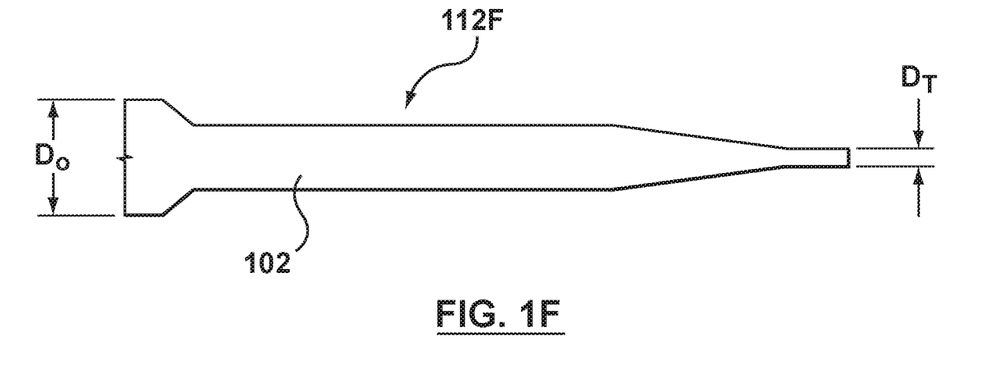
FIG. 1F is a side view illustrating another embodiment of a distal tip portion of a guidewire.

Distal tip portion 112 is also formed from the coextruded or composite wire having outer layer 104 and a solid or continuous inner core 106, as shown in the sectional view of FIG. 1D. The outer diameter of guidewire shaft 102 along distal tip portion 112 is tapered in order to be very flexible or "floppy" and capable of conforming to and following the contours of highly tortuous vascular anatomy. More particularly, as shown in FIG. 1D, the outer diameter of guidewire shaft 102 decreases in a distal direction from outer diameter $D_O$ to a distal tip diameter $D_T$. In one embodiment shown in FIG. 1C, inner core material 106 continuously tapers in a distal direction to create the tapered distal tip portion 112 while the thickness of outer layer 104 remains approximately constant. However, as will be understood by those of ordinary skill in the art, distal tip portion 112 may have other constructions which result in a flexibility suitable for accessing vascular anatomy without damage thereto. In embodiments hereof, the distal tip portion may alternatively include a stepped taper as shown in FIG. 1F. More particularly, distal tip portion 112F includes a guidewire shaft 102 in which the outer diameter decreases in a distal direction from outer diameter $D_O$ to a distal tip diameter $D_T$ in a stepped or incremental manner. In an embodiment, tapered distal tip portion 112F may be supplemented with a polymer coating or jacket that makes the outer diameter of guidewire shaft 102 constant along the length of tapered distal portion 112F. In another embodiment of the distal tip portion depicted in FIG. 1E, a distal tip portion 112E includes a helical element or coil 122 attached to and extending about tapered distal portion 112E of guidewire shaft 102. The portion of guidewire shaft 102 that extends within coil 122 may include both inner core material 106 and outer layer 104, although the layers are not shown in FIG. 1E. The portion of guidewire shaft 102 that extends within coil 122 acts as a core or inner member for coil 122 and the presence of coil 122 results in distal region of increasing flexibility that is adapted to follow the contours of the vascular anatomy while still being capable of transmitting rotation from the proximal end of the guidewire to the distal end, so that the physician can controllably steer the guidewire through the patient's blood vessels. The portion of guidewire shaft 102 that extends within coil 122 may have a smaller outer diameter than the remainder of guidewire 102. In an embodiment (not shown), the portion of guidewire shaft 102 that extends within coil 122 may include an inner core material that continuously or incrementally tapers in a distal direction as described above with respect to FIG. 1D and FIG. 1F such that the portion of guidewire shaft 102 that extends within coil 122 is tapered. The end or tip of the distal tip portion may be rounded as shown in FIG. 1D, may include a separate semi-circular tip component 124 as shown in FIG. 1E, or alternatively may be relatively blunt or pointed as shown in FIG. 1F. Further, although shown as integrally formed with guidewire shaft 102, in another embodiment (not shown), the distal tip portion may be a separate component that is mechanically coupled to guidewire shaft 102.

Referring now to the sectional view of FIG. 1B, marker portion 110 includes outer layer 104 and a non-continuous inner core 106 that forms the plurality of integral radiopaque markers 118. Marker portion 110 is formed by exposing guidewire shaft 102 to the erosion agent, which accesses inner core 106 via a plurality of openings or channels 114. Channels 114 are holes which extend through outer layer 104 in order to expose inner core 106 and are longitudinally spaced along marker portion 110. When guidewire shaft 102 is exposed to the erosion agent, the erosion agent erodes finite amounts of the inner core material adjacent to each channel 114, thereby removing segments of the inner core material adjacent to each channel 114 and forming voids 116. Integral radiopaque markers 118 are thereby formed by the remaining segments of the inner core material which are positioned between voids 116. The pattern or sequence of voids 116 and integral radiopaque markers 118 provide a means of in situ measurement when viewed under fluoroscopy.

In one embodiment, marker portion 110 may be between 20 cm and 40 cm in length and is positioned just proximal to distal tip portion 112, which may range between 5 cm and 20 cm in length depending on the application. Guidewire 102 thus includes three portions of increasing flexibility, with proximal portion 108 having the least flexibility, distal tip portion 112 having the most flexibility, and intermediate marker portion 108 sandwiched therebetween. The overall length of guidewire 100 may be between 180 cm and 300 cm.

Guidewire 102 is exposed to the erosion agent for a predetermined amount of time to result in a desired/predicted length of each void 116. More particularly, the rate of erosion of the inner core material is known and predictable for a particular combination of materials. The amount of time which guidewire shaft 102 is exposed to the erosion agent thus depends upon the materials chosen for inner core 106 and the erosion agent. In addition, the spacing between each channel 114 is selected or designed based on the desired/predicted length of radiopaque markers 118 and the desired/predicted length of each void 118. Accordingly, by controlling the amount of time which guidewire 102 is exposed to the erosion agent, accurate and distinct marker spacing may be achieved. In one embodiment shown in FIG. 1B, the size of voids 116 are relatively smaller than the size of markers 118. By minimizing the size of voids 116 relative to the size of markers 118, guidewire 100 maintains its structural integrity while providing a series of integral radiopaque markers therein for in situ measurement. However, it will be understood by those of ordinary skill in the art that the above-described dimensions of marker portion 110, radiopaque markers 118, voids 116, and other components of guidewire 100 are exemplary and may vary according to application. For example, in one embodiment shown of marker portion 110C shown in FIG. 1C, the size of markers 118C are relatively smaller than the size of voids 116C. In an embodiment, each radiopaque marker 118C may be approximately 2 mm in length and each void 116C may be approximately 8 mm in length. The consecutive application of markers and voids at this spacing yields radiopaque markers spaced at 10 mm from marker center to marker center. By minimizing the size of markers 118C relative to the size of voids 116C, marker portion 110C provides a series of integral radiopaque markers for in situ measurement while having increased flexibility due to the relatively larger size of voids 116C. In yet another embodiment (not shown), the size of each radiopaque marker may be approximately equal to the size of each void. In relative terms, the length of each radiopaque marker may be between 20% and 150% of the length of each void. The relative sizes of each radiopaque marker and each void depend upon the desired flexibility of the marker portion for a particular application.

Figure 2:
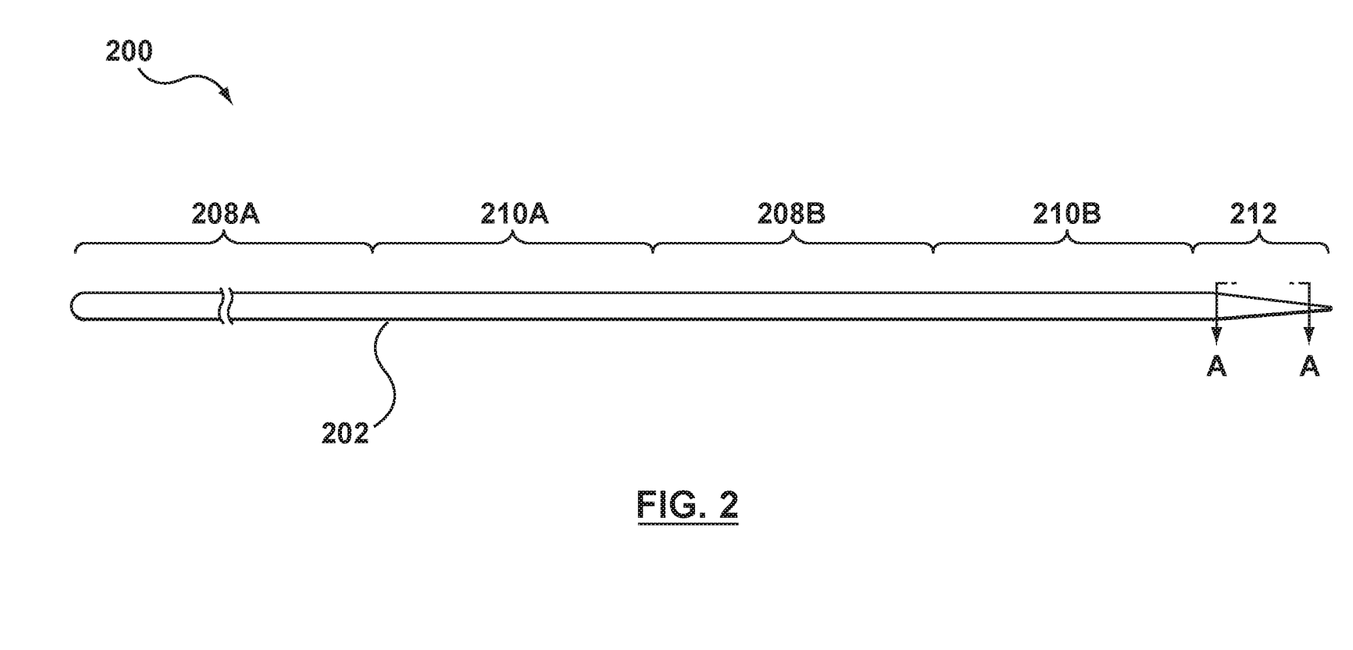
FIG. 2 is a side view of an embodiment of a guidewire having multiple marker portions, each marker portion including a plurality of integral radiopaque markers.

In addition, although FIG. 1 illustrates a guidewire having a single marker portion having a series of radiopaque markers, it will be understood by those of ordinary skill in the art that multiple marker portions may be formed along the length of the guidewire if desired. For example, as shown in FIG. 2, a guidewire 200 is shown having two marker portions 210A, 210B spaced apart along the length of guidewire 200. Each marker portion 210A, 210B include a non-continuous inner core forming a series of radiopaque markers (not shown in FIG. 2) and voids (not shown in FIG. 2) therebetween, as described above with respect to FIG. 1B.

Marker portion 210B is positioned just proximal to distal tip portion 212, while marker portion 210A is positioned between two proximal portions 208A, 208B. Having multiple marker portions along the length of guidewire 200 provides additional means of in situ measurement. Since marker portions are formed by eroding segments of inner core material, it will be understood by those of ordinary skill in the art that integral radiopaque markers may advantageously be formed at essentially any location on the guidewire. Multiple marker portions, each having different spacing between and/or length(s) of radiopaque markers, may selectively be placed along the length of the guidewire shaft.

Figure 3:
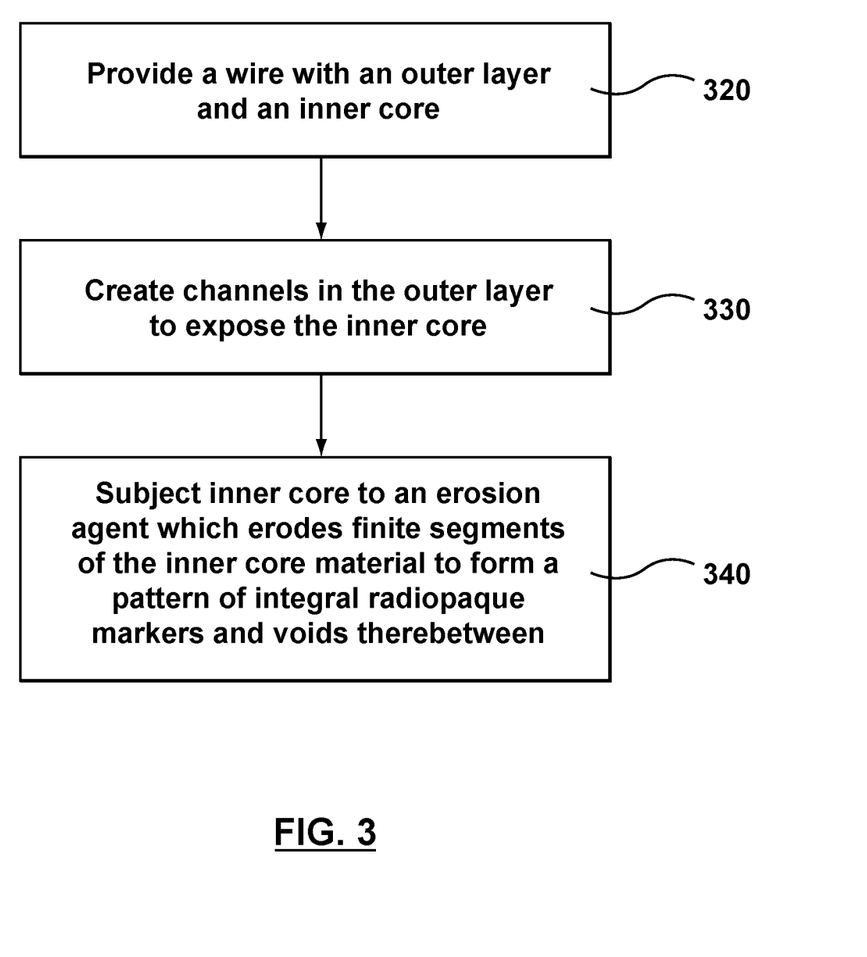
FIG. 3 is a flow chart illustrating an embodiment of a method of manufacturing a guidewire having a marker portion with a plurality of integral radiopaque markers.

FIG. 3 is a flow chart illustrating a method of manufacturing guidewire 100 having integral radiopaque markers 118. An initial step 320 includes providing a coextruded or composite elongated wire having outer layer 104 and inner core 106 which forms the basis of guidewire shaft 102. Such a coextruded or composite wire may be formed by any method known in the art, for example and not by way of limitation, a drawn filled tubing process, extruding the outer layer over the inner core, or any other suitable method. Examples of such wires and methods of forming such wires can be found in U.S. Pat. No. 5,630,840 to Mayer, U.S. Pat. No. 6,248,190 to Stinson, U.S. Pat. No. 6,497,709 to Heath, and U.S. Pat. No. 7,101,392 to Heath, each of which is incorporated by reference herein in its entirety.

Step 330 of FIG. 3 is creating openings or channels 114 in outer layer 104 in order to expose inner core 106. Channels 114 may be selectively formed at any location along the length of guidewire shaft 102 that is to include radiopaque markers. As discussed above with respect to FIG. 2, guidewire 100 may include multiple marker portions along the length thereof with each marker portion including a plurality of integral radiopaque markers. Referring back to FIG. 1B, two longitudinally-aligned rows of channels 114 are positioned on opposing sides of guidewire shaft 102 such that the rows are positioned approximately 180 degrees apart. As described above, the spacing between channels 114 may vary depending upon application but should be spaced apart as desired to form radiopaque markers suitable for in situ measurement. Channels 114 may be laser cut, drilled, etched, or otherwise provided in outer layer 104 and have a depth at least equal to the thickness of outer layer 104. In addition, channels 114 may have a circular, oval, rectangular, or any other suitable cross-section and in one embodiment, may have a diameter or width that ranges between a few and hundreds of microns, up to ½ of the outer diameter of guidewire 100.

In order to form radiopaque markers 118, guidewire shaft 102 is subjected to an erosion agent that erodes segments of the inner core material to form a pattern of integral radiopaque markers 118 and voids 116 therebetween as shown in step 340. The erosion agent accesses inner core 104 via channels 114 and erodes finite amounts or segments of the inner core material adjacent to channels 114. In one embodiment, the material for inner core 106 is tungsten or rhenium, the material for outer layer 104 is NiTi (Nitinol), and the erosion agent is xenon difluoride gas. In another embodiment, the material for outer layer 104 is MP35N. The material of inner core 106 (tungsten or rhenium) is eroded by subjecting guidewire shaft 102 to xenon difluoride gas in a vacuum which reacts with the core material to form a gas that can be exhausted from the guidewire shaft via channels 114. However, xenon difluoride gas does not react with NiTi (Nitinol) or MP35N such that the outer layer 104 remains after segments of the inner core 106 have been removed, leaving the structure shown in FIG. 1B. Alternatively, bromine trifluoride or other interhalogen gases can be used as the erosion agent instead of xenon difluoride.

In one embodiment, channels 114 may be closed or filled in after radiopaque markers 118 are formed. Channels 114 may be filled as a separate manufacturing step, or may be filled in during application of a low-friction coating applied to the outer surface of guidewire 100, such as a coating of PTFE. With channels 114 filled in or covered, any discontinuities in the outer surface of guidewire 100 are eliminated, thereby eliminating or minimizing performance-related issues with 'catching' or friction of a treatment device slid or tracked over the outer surface of guidewire 100. In another embodiment, channels 114 may be left open after radiopaque markers 118 are formed. Channels 114 may be of a sufficiently small diameter that the edges thereof do not create surface discontinuities of concern. Leaving channels 114 open minimizes manufacturing costs and may increase the flexibility of the guidewire in the marker portion. For example, the diameters of channels 114 may be sized appropriately to make marker portion 110 of guidewire 100 more flexible.

Other examples of outer layer, inner core, and erosion agent combinations include but are not limited to an outer layer of Nitinol or stainless steel, an inner core of gold, and an erosion agent of potassium triiodide. These examples are illustrative and it would be understood by one skilled in the art that an erosion agent that reacts with the material of the inner core to erode the core material but does not react with the material of an outer layer may be used in step 340 to form a series of integral radiopaque markers within guidewire 100. For example, co-pending U.S. application Ser. No. 12/500,359, filed Jul. 9, 2009, U.S. Provisional Application No. 61/244,049, filed Sep. 20, 2009, U.S. Provisional Application No. 61/244,050, filed Sep. 20, 2009, and co-pending U.S. application Ser. No. 12/884,551, filed Sep. 17, 2010, each incorporated by reference herein in their entirety, disclose methods for forming drug-eluting stents with hollow struts. In the stent embodiments described, the hollow struts are formed from a composite wire or member including an outer member and a core member, wherein the core member is a sacrificial material that is removed after shaping the composite wire into a desired shape. It will be understood by those of ordinary skill in the art that combinations of the inner member, the outer member, and the erosion agent and manufacturing steps for removing the core member described in the above-mentioned patent applications may be utilized in forming a guidewire having a series of integral radiopaque markers as described herein.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A guidewire comprising:
an elongated shaft having an outer layer which is disposed over and encloses an innermost core, an inner surface of the outer layer abutting against an outer surface of the innermost core for an entire length of the innermost core, wherein the innermost core is formed from a radiopaque material susceptible to erosion by an erosion agent and the outer layer is formed from a material not susceptible to erosion by the erosion agent,
wherein the innermost core is solid and continuous along a proximal portion of the shaft, and
wherein the innermost core is non-continuous along a marker portion of the shaft and includes a plurality of segments of the radiopaque material with a plurality of voids therebetween such that each void extends between two adjacent segments of the radiopaque material, the marker portion being distal to the proximal portion of the shaft.

2. The guidewire of claim 1, wherein the marker portion includes a plurality of channels formed through the outer layer and the plurality of voids are adjacent to the plurality of channels.

3. The guidewire of claim 1, wherein the innermost core is solid and continuous along a distal tip portion of the shaft, the distal tip portion being distal to the marker portion.

4. The guidewire of claim 3, wherein an outer surface of the distal tip portion is tapered.

5. The guidewire of claim 3, wherein the proximal portion is the least flexible portion of the guidewire and the distal tip portion is the most flexible portion of the guidewire.

6. The guidewire of claim 1, wherein the radiopaque material is selected from the group consisting of tungsten, tantalum, platinum, platinum and iridium, rhenium, and gold.

7. The guidewire of claim 1, wherein each segment of the radiopaque material is between 20% and 150% of a length of each void.

8. A guidewire formed from an elongated shaft, at least a portion of the shaft comprising:
an outer layer formed from a material non susceptible to erosion by an erosion agent; and
an innermost core formed from a radiopaque material susceptible to erosion by the erosion agent, the outer layer being disposed over and enclosing the innermost core and an inner surface of the outer layer abutting against an outer surface of the innermost core for an entire length of the innermost core, wherein at least a portion of the innermost core is non-continuous and includes a series of a plurality of radiopaque markers with a plurality of voids therebetween such that each void extends between two adjacent radiopaque markers.

9. The guidewire of claim 8, wherein a portion of the innermost core is solid and continuous along a distal tip portion of the shaft, the distal tip portion being distal to the radiopaque markers.

10. The guidewire of claim 9, wherein the distal tip portion is the most flexible portion of the guidewire.

11. The guidewire of claim 8, wherein a portion of the innermost core is solid and continuous along a proximal portion of the shaft, the proximal portion being proximal to the radiopaque markers.

12. The guidewire of claim 8, wherein each radiopaque marker is between 20% and 150% of a length of each void.

13. A guidewire formed from an elongated shaft, at least a portion of the shaft comprising:
an elongated shaft having an outer layer which is disposed over and encloses an innermost core, an inner surface of the outer layer in intimate contact with an outer surface of the innermost core for an entire length of the innermost core, wherein the innermost core is formed from a radiopaque material susceptible to erosion by an erosion agent and the outer layer is formed from a material not susceptible to erosion by the erosion agent,
wherein the guidewire includes a proximal portion, a marker portion, and a distal tip portion, the marker portion being between the proximal portion of the guidewire and the distal tip portion of the guidewire, and
wherein the innermost core is solid and continuous along the distal tip portion of the guidewire, the innermost core is non-continuous along the marker portion of the guidewire and includes a plurality of integral radiopaque markers with a plurality of voids therebetween such that each void extends between two adjacent integral radiopaque markers, and the innermost core is solid and continuous along the proximal portion of the guidewire, and
wherein each void of the plurality of voids is devoid of the radiopaque material of the innermost core for an entire length of the respective void.

14. The guidewire of claim 13, wherein the outer layer and the innermost core of the elongated shaft are coextruded.

15. The guidewire of claim 13, wherein the outer layer and the innermost core of the elongated shaft are a composite elongated wire.

16. The guidewire of claim 13, wherein the outer layer is selected from the group consisting of a stainless steel alloy, a chromium cobalt alloy, and a nickel titanium alloy and the radiopaque material is selected from the group consisting of tungsten, tantalum, platinum, platinum and iridium, rhenium, and gold.

17. The guidewire of claim 13, wherein an outer surface of the distal tip portion is tapered and the proximal portion of the guidewire is the least flexible portion of the guidewire and the distal tip portion of the guidewire is the most flexible portion of the guidewire.

18. The guidewire of claim 13, wherein each integral radiopaque marker is between 20% and 150% of a length of each void.

19. The guidewire of claim 13, wherein the marker portion of the guidewire includes a plurality of channels formed through the outer layer and the plurality of voids are adjacent to the plurality of channels.

20. The guidewire of claim 19, wherein the plurality of voids are formed by removal of finite segments of the innermost core after the innermost core is subjected to an erosion agent through the plurality of channels, with each finite segment of the innermost core removed by the erosion agent forming a void between two adjacent integral radiopaque markers.

* * * * *